United States Patent [19]

Owens et al.

[11] Patent Number: 4,972,846
[45] Date of Patent: Nov. 27, 1990

[54] PATCH ELECTRODES FOR USE WITH DEFIBRILLATORS

[75] Inventors: William M. Owens; Leonard G. Marlow, Jr., both of Flagstaff, Ariz.

[73] Assignee: W. L. Gore & Associates, Inc., Newark, Del.

[21] Appl. No.: 304,684

[22] Filed: Jan. 31, 1989

[51] Int. Cl.$^5$ ............................ A61N 1/05; A61N 1/39
[52] U.S. Cl. .................................... 128/784; 128/798; 128/419 D
[58] Field of Search ................... 128/784, 798, 419 D, 128/419 P

[56] References Cited

U.S. PATENT DOCUMENTS

| | | | |
|---|---|---|---|
| 3,953,566 | 4/1976 | Gore . | |
| 4,030,509 | 6/1977 | Heilman et al. | 128/784 X |
| 4,291,707 | 9/1981 | Heilman et al. | 128/784 X |
| 4,499,907 | 2/1985 | Kallok et al. | 128/786 |
| 4,573,483 | 3/1986 | Hirschberg | 128/784 |
| 4,576,174 | 3/1986 | Miyazaki et al. | 128/784 X |
| 4,641,656 | 2/1987 | Smits | 128/419 D |
| 4,662,377 | 5/1987 | Heilman et al. | 128/419 D |
| 4,690,155 | 9/1987 | Hess | 128/786 |
| 4,827,932 | 5/1989 | Idekar et al. | 128/419 D |

FOREIGN PATENT DOCUMENTS

| | | |
|---|---|---|
| 0280564 | 8/1988 | European Pat. Off. . |
| 2588758 | 4/1987 | France . |
| WO82/02664 | 8/1982 | PCT Int'l Appl. . |
| 2182566 | 5/1987 | United Kingdom .......... 128/419 D |

OTHER PUBLICATIONS

D. Santel, et al., Implantable Defibrillator Electrode System: A Brief Review PACE vol. 8, Jan.-Feb. 1985, pp. 123-131.

*Primary Examiner*—Lee S. Cohen
*Attorney, Agent, or Firm*—Dena M. Weker

[57] ABSTRACT

A patch electrode for use with defibrillators is provided. The patch electrode comprises a soft, flexible patch of polymeric material and bonded to it, a smaller patch of polymeric material that has been metal-plated. A lead wire is attached to the patch by a polymeric boot. A defibrillator system is also provided wherein two electrodes and lead wires are attached to a generator typically used for cardioventing and defibrillization. The invention is particularly useful for cardiac muscle stimulation but can also be used for muscle stimulation.

16 Claims, 4 Drawing Sheets

PATCH ELECTRODES FOR USE WITH DEFIBRILLATORS

FIELD OF THE INVENTION

The present invention relates to a novel patch electrode for use with defibrillators. The patch electrode includes a soft, flexible patch of polymeric material and a lead wire attached to the patch by a polymeric boot. The lead wire is further attached to a generator typically used for cardioverting and defibrillization. The invention is particularly useful for cardiac muscle stimulation but also can be used for any muscle stimulation.

BACKGROUND OF THE INVENTION

Each year, approximately 400,000 to 600,000 Americans suffer from cardiac arrythmia such as tachyarhythmia which often worsens into ventricular fibrillation in which the heart twitches furiously but pumps no blood, usually causing sudden death. Defibrillation is referred to as the non-synchronized delivery of electrical energy to the heart to correct ventricular fibrillation.

Research in the field of cardioverters/defibrillators has been in progress for many years.

U.S. Pat. No. 4,499,907 describes a transvenous cardioversion lead which is adapted for use with presently available external defibrillation units. The lead is provided with circuitry which reduces energy from the defibrillator to a safe level for use with transvenous defibrillation. The lead has four electrodes, of which two are implanted within the right ventricle of the heart and the other two implanted within the superior vena cava.

U.S. Pat. No. 4,641,656 describes a four-electrode lead system designed to maximize the efficiency of electrical energy and depolarizing the heart and terminating tachycardia or defibrillation. The electrodes are described to be mounted around the heart wherein the regime for applying pulses and optimizing electrode size and placement are altered to provide a more efficient system.

U.S. Pat. No. 4,690,155 describes a monophasic action potential contact electrode catheter for use in the study of the electrophysiology of cardiac tissue. The catheter includes an elongated tubular body having a hub assembly at its proximal end portion and a distal tip portion.

U.S. Pat. No. 4,662,377 describes an automatic implantable cardioverter/defibrillator having an electrode system which includes an intravascular catheter with a first electrode adjacent the distal end of the catheter, and a second electrode at the proximal end. The catheter electrode is inserted intravenously to a position such that the distal electrode is positioned in the right ventricular apex of the heart and the proximal electrode is positioned in the superior vena cava region of the heart.

A flexible patch electrode is also electrically connected to the proximal electrode and subcutaneously positioned inside the thoracic cavity. The patch electrode is described as being flexible, conformal, generally planar having a metallic mesh on the surface facing the heart.

Many of the references cited require implantation of electrodes within the thoracic cavity and myocardium thus subjecting a patient to the surgical opening of the thoracic cavity and possible risks of infection. Also, many of the cardioverter/defibrillator systems require large discharges of electrical energy to the heart (10 joules or more). Furthermore, many will not maintain close contact with the endocardium, requiring higher electrical energy and, or causing burning of the cardiac tissue.

There is a need for a flexible, compliant defibrillation patch and system capable of maintaining close contact of the electrode material to muscle tissue, thereby requiring lower energy discharges (four+joules) without burning muscle tissue.

SUMMARY OF THE INVENTION

The present invention provides a patch electrode for use with defibrillators made of an outer insulating membrane of porous polymeric material, an inner metalized membrane also made of a porous polymeric material plated with a metal, such as platinum or gold and means for bonding the inner polymeric membrane to the outer polymeric membrane so that a border of the outer membrane surrounds and abuts said inner membrane. The preferred material for use in both membranes comprising the patch electrodes is expanded PTFE however other polymeric materials such as silicones, polyurethanes, polyethylenes, polysulfones, polyacrylics, polycarboxylates, polyesters, polypropylene, poly(hydroxyethyl) methacrylate and perfluorinated polymers are also suitable.

The patch electrodes may be of various shapes such as a tear drop, hourglass, or inverted U.

The invention also provides a defibrillator system for delivering electrical shocks to a muscle, including heart muscle of a patient comprising two patch electrodes each further comprising an outer insulating membrane of a porous polymeric material, an inner membrane having a metal surface, two lead wires, each having a center conductor surrounded by at least one layer of insulation and adhesively affixed to individual electrodes to form a conductive connection further reinforced by a silicone boot and a pulse generator means having anode and cathode terminals to which the lead wires are connected.

DETAILED DESCRIPTION OF A THIN PREFERRED EMBODIMENT

The following description provides examples for use of the patch electrode system for cardiac muscle stimulation. It is believed however that the patch electrode system may be applied to any type of subcutaneous or external muscle stimulation in addition to cardiac muscle. The system may also be applicable to bone growth stimulation, heart pacing or a variety of other uses requiring electrical signal interface.

Figure 1:
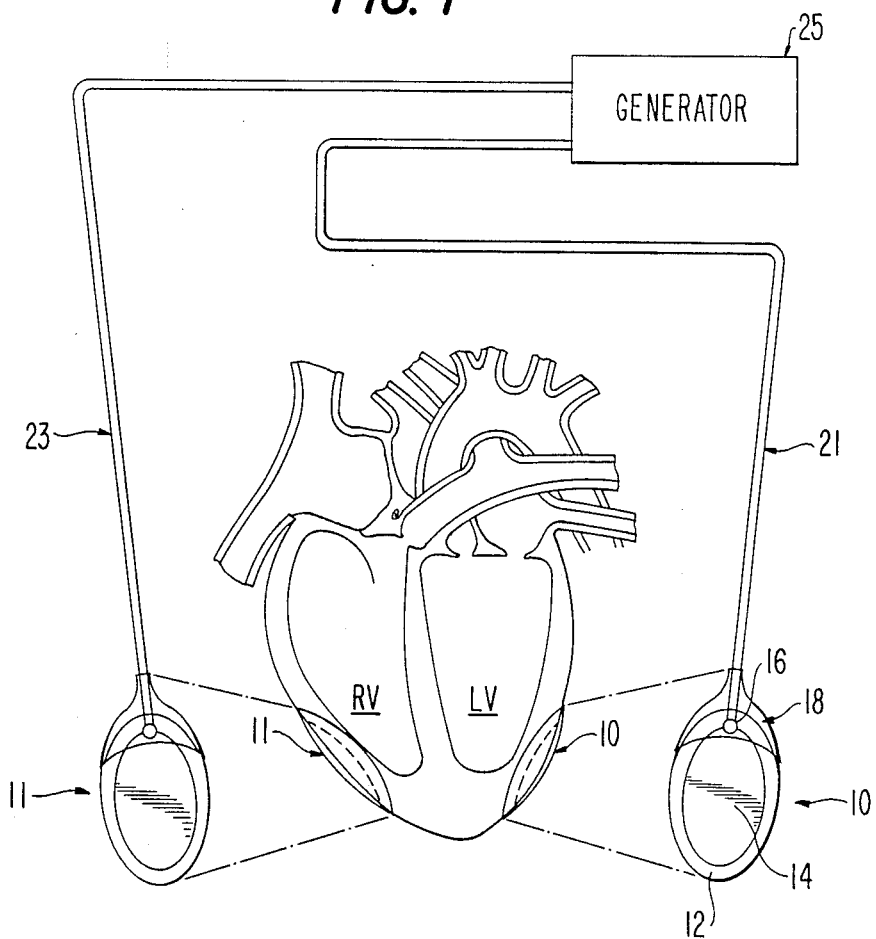
FIG. 1 illustrates a plan view of one embodiment of the electrode patch system according to the present invention.

With reference to FIG. 1, a pair of flexible patch electrodes, 10 and 11, are provided. One patch electrode serves as the anode of the system and is positioned over the right ventricle, so that it is inside the thoracic cavity and outside the myocardium.

Figure 2:
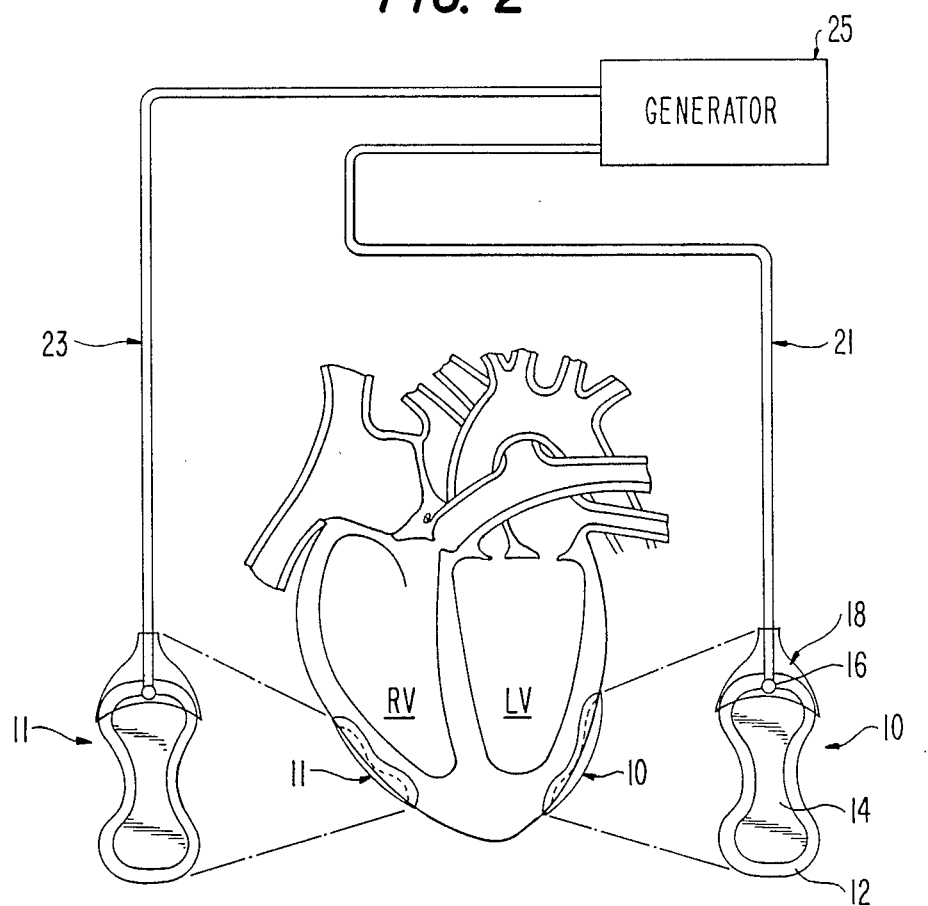
FIG. 2 illustrates a plan view of an hourglass electrode patch, a second embodiment according to the present invention.
Figure 3:
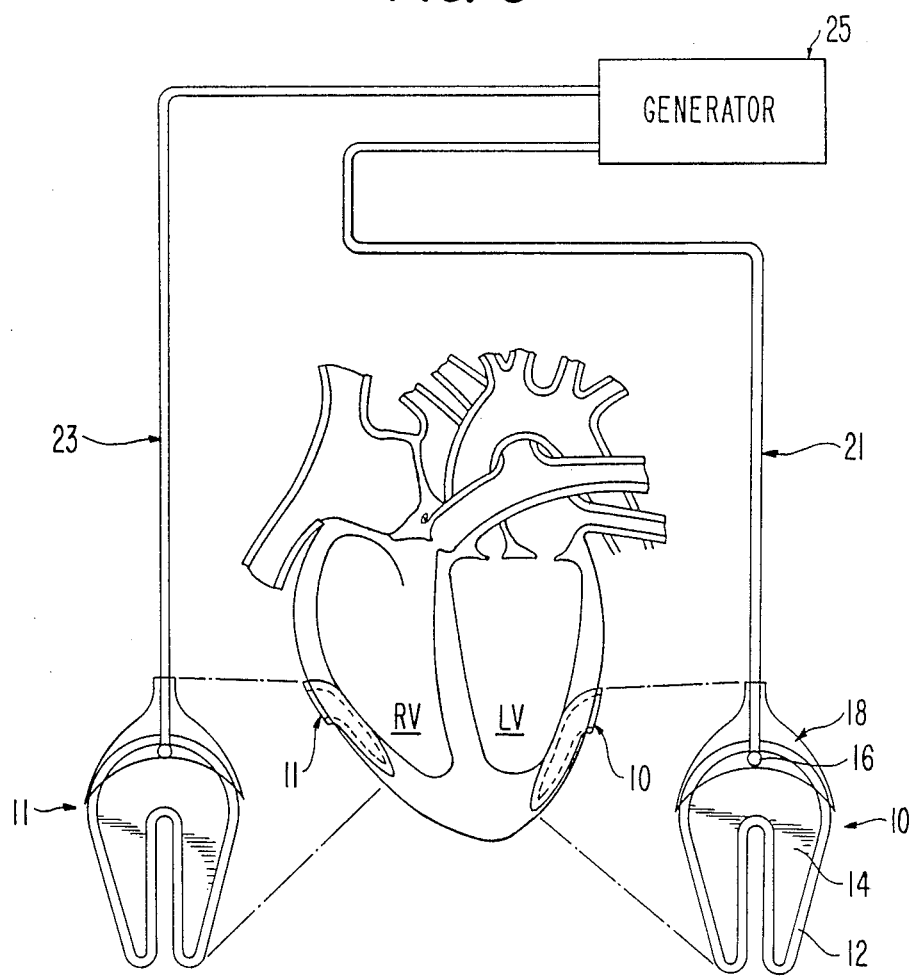
FIG. 3 illustrates a plan view of a horseshoe electrode patch, a third embodiment according to the present invention.

The second patch electrode serves as the cathode of the system and is positioned over the left ventricle, so that it is inside the thoracic cavity and outside the myocardium. FIGS. 1, 2 and 3 also show the location on the heart where the electrodes are to be attached.

The patch electrode is comprised of two layers, an outer insulating layer 12, and an inner metallic layer 14. The outer layer 12 is comprised of a porous polymeric material. A preferred porous polymeric material is expanded polytetrafluoroethylene {hereinafter PTFE} having a microstructure of nodes and fibrils such as that described in U.S. Pat. Nos. 3,953,566 and 4,897,390 or may be comprised of other porous PTFE materials such as that described in U.S. Pat. No. 4,082,893. Alternatively, other biocompatible, porous polymeric materials including silicones, polyurethanes, polyethylenes, polysulfones, polyacrylics, polycarboxylates, polyesters, polypropylene, poly(hydroxyethyl)methacrylates, and perfluorinated polymers. The important criteria is that the material is able to be a good insulator. The thickness of the outer insulting layer should be preferably less than 0.1 mm, and is most preferably less than 0.08 mm. Furthermore, for an outer insulating material made of expanded PTFE, the maximum fibril length should be 10 microns or less to prevent tissue ingrowth but allow for tissue attachment.

Within the outer insulating layer 12 is an inner metallic layer 14. This inner layer may be comprised of a wire mesh or preferably a metalized conductive polymeric material capable of carrying a current and which is sufficiently pliable so that when flexed repeatedly the metalized conductive material remains intact. Any conductive metal may be used, however, a most preferred metalized polymeric material includes expanded PTFE as described above plated with gold. Preparation of such a material is described in Example 1. Alternatively, expanded PTFE plated with platinum is also suitable. Such a metalized material is described in U.S. Pat. Nos. 4,557,957 and 4,720,400.

The thickness of the inner layer should be preferably at least 0.25 mm thick and is most preferably between 0.8 mm and 1.0 mm. For the inner layer made of PTFE onto which metal has been applied and for efficient plating the fibrils should be about 30 microns and is preferably between 50-60 microns.

The outer and inner layers are bonded together by a thin application of a polymeric adhesive between them.

Figure 1A:
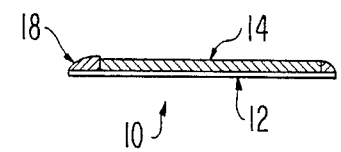
FIG. 1a illustrates a cross-section of one embodiment of the electrode patch.

FIG. 1 shows the defibrillator system having two tear-drop shaped defibrillator patches. FIG. 2 shows the defibrillator system having two patches each in the shape of an hourglass. FIG. 3 shows the defibrillator patch having an inverted U-shaped configuration. Any of these shapes as well as other shapes are all suitable for the defibrillator system so long as they are flexible and capable of withstanding repeated contractions and twists as the heart contracts and twists. The size of the patch should be of sufficient size to totally saturate the heart with high voltage but not so low as to cauterize the heart or tissue surrounding the heart with higher current densities. FIG. 1a shows a cross-section of the electrode patch indicating the outer and inner membranes and the bonding between them.

Figure 4:
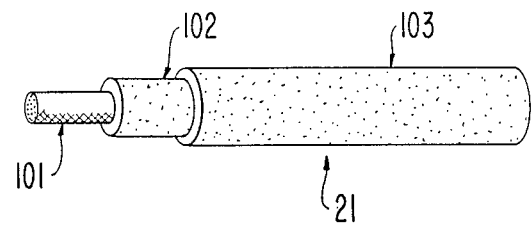
FIG. 4 illustrates a cross-sectional planar view of the lead wire used in the present invention.

The lead wires 21 and 23 shown in FIGS. 1, 2 and 3 used to connect the patches to the generator may be any conventional low electrical resistance wire surrounded by several layers of polymeric insulation. FIG. 4 shows a cross-section of the preferable configuration of the lead wire. A preferable lead wire system includes a center conductor wire 101 of drawn braided silver surrounded by a first layer of low density expanded PTFE 102 and surrounded again by a second layer of high density expanded PTFE 103 which may be impregnated with either silicone or polyurethane. Other suitable wires include chromium based wires. The preferable insulation material of expanded PTFE is the same material that also comprises the defibrillator patches. The low density expanded PTFE has a density range of preferably 0.7–1.03 g/cc to provide high flexibility and the high density expanded PTFE has a density range of preferably 1.2 to 1.3 g/cc to provide an impermeable barrier.

The lead wire 23 is attached to the defibrillator patch with the use of a commercially available low resistance conductive epoxy 16 or may be ultrasonically welded together. One commercially available conductive epoxy is Eccobond ® solder available from W.R. Grace in Woburn, Mass.

Further covering a portion 18 of the defibrillator patch 10 and lead wire 21 is a silicone boot which reinforces the connection made between the patch and wire. The silicone boot is a glue which hardens in a short period of time. This material is commercially available from Dow Corning MDX4-4210 medical grade elastomer, Dow Corning Corporation, Midland, Mich.

In operation by reference to FIG. 1, the generator issues a high energy shock by providing a voltage pulse across the distal electrode patch 11 and proximal electrode patch 10. Preferably, the high energy pulse is an exponentially decaying truncated voltage. An electric field is created across the heart that more effectively depolarizes the heart using electrical energies in the 4 to 7 joule range rather than the higher energy levels required by existing systems. If unsuccessful, additional pulses may be issued, which may be increased at high energy levels such as up to 50 joules.

EXAMPLE 1

A defibrillator system was made having two electrode patches with tear-drop shape configurations similar to that shown in FIG. 1.

The outer patch was first made by obtaining a membrane of expanded PTFE, specifically a GORE-TEX ™ Surgical Membrane, commercially available from W. L. Gore & Associates, Inc. This material was made in accordance to the teachings of U.S. Pat. Nos. 3,953,566 and 4,187,390. The thickness of the membrane was between 0.08 mm and 0.1 mm. The membrane had a microstructure comprising nodes and fibrils. The fibrils had a length of about 10 microns.

The fibril length of expanded PTFE is defined herein as the average of ten measurements between nodes connected by fibrils in the direction of expansion. In order to measure the average fibril length of expanded PTFE, two parallel lines are drawn across a photomicrograph of about 100 times magnification of the surface of the material so as to divide the photograph into three equal areas. If the material has been uniaxially expanded, these lines are drawn in the direction of expansion (i.e. direction of orientation of fibrils). Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the right hand side of the photograph. If the material is expanded in more than one direction, the lines are drawn and fibril lengths measured as above, except when a node is not attached by fibrils to a node intersecting the drawn line. In this case, the fibril length from the node to a node which creates the least angle with the drawn line is measured along the fibril's axial orientation. The ten measurements obtained by this material are averaged to obtain the average fibril length of the material. For the outer patch, the fibril length had a length of about 10 microns.

The second layer of the patch was made with a second membrane of expanded PTFE, plated with gold. This membrane was made similar to the inner layer, and in accordance to the teachings of U.S. Pat. Nos. 3,953,566 and 4,187,390. The microstructure of this membrane also consisted of nodes and fibrils but had fibril lengths approximately of 30 microns.

This membrane was plated through the entire cross-section with copper using an electroless process system, of which all of the referenced chemicals are commercially from Shipley Corporation. Newtown, Mass. Similar electroless systems commercially available from other manufacturers may be substituted. For the present example, the membrane was first dipped in a cleaner-conditioner 230 at a temperature of 160°–180° F. for 20 minutes. The membrane was then dipped in Cataprep ® 404 at a temperature of 75–100° F. for a period of 60–90 seconds. A layer of palladium-tin is then applied to the membrane by dipping the treated membrane in Cataposit ® 44 at a temperature of 100–120° F. for a period of 2–4 minutes. The tin is then removed by dipping the membrane in Accelerator 240 at a temperature of 90–115° F. for a period of 2–3 minutes with agitation at a rate of 3–5 strokes per minute. Finally, the membrane is copper plated by dipping in Cuposit ® 250 electroless copper at a temperature of 95–125° F. for about 12–20 minutes or until the desired copper deposition is achieved. Alternatively, the copper bath may be air agitated with compressed nitrogen.

The membrane was finally plated with gold using an electro-plating system including a platinum plated electrode as an anode and an adjustable DC power supply. The membrane was attached to the cathode. Deposition was achieved on the membrane when the anode was submerged in Orostrike gold, commercially available from Technic, Inc. of Cranston, R.I., a gold solution heated to a temperature of about 80–140° F. until gold deposition had occurred, the period of time of approximately 18 minutes. The membrane was plated with sufficient gold to produce a resistance of approximately 1 ohm or less on the surface of the membrane. The final metalized membrane was rinsed in distilled water baths and freon baths to remove chemical residue. Other metallized systems are also suitable. Times and temperatures may also vary. The metalized membrane was coated with a polymeric adhesive, such as medical grade elastomer silicone MDX4-4210 or Silastic ® 382 both commercially available from Dow Corning, Midland, Mich. The coated membrane was placed in a vacuum chamber at 18 inches of mercury for 30 minutes to draw the silicone within and around the node-fibril microstructure of the membrane and the area of the lead wire connected to the metalized membrane. Penetration of the membrane by the silicone was about 90%. The silicone was then cured to insure a hermetic seal of the lead connection and fibril-node plating surface. The polymeric penetration and encapsulation provides strain relief to the plated nodes and fibrils to prevent cracking of the plating surface during flexing and to maintain capacitative resistance.

The metalized polymeric layer was then bonded to the outer insulating layer with a thin layer of silicone. The metalized layer was centered on the outer insulating layer so that there was at least a 6.4 mm rim around the metalized membrane.

The lead wire used to connect the patch to the defibrillator comprised a drawn braided silver conductor of 0.38mm was first coated with expanded PTFE having a density of about 0.7–0.9 g/cc and then extrusion coated with a second layer of expanded PTFE having a density of 1.2 to 1.3 g/cc. The overall diameter was about 1.4 mm. A gold connector was crimped to the lead wire and then bonded to the metalized polymeric with a conductive epoxy, Eccobond solder commercially available from Emmerson and Cuming, Canton, Mass. The final lead wire was approximately 61 cm long.

The assembly was completed by installation of a preformed silicone boot that encapsulated part of the lead wire, the junction of lead wire and membrane, and a section of both membrane layers. A layer of silicone was applied over the rim of the outer insulating rim, adjacent to the metalized layer of sufficient amounts so that the overall patch creates a flat surface.

The final assembly was sufficient to produce a lead-patch assembly having a resistance of less than 10 ohms from the metalized patch surface through and to the end of the lead wire. The opposite end of the lead wire was connected to an external cardioverter/defibrillator having an adjustable threshold regulator and an external trigger button.

EXAMPLE 2—ACUTE DOG STUDY

A defibrillator system was made such as that described in Example 1. The patches were implanted in a dog wherein the inner layer of each patch was next to the myocardium. One patch, serving as the anode, was sutured in place in the area over the right ventricle. A second patch, serving as the cathode was implanted in the area of the left ventricle. Threshold was determined by the pre-set threshold regulator. Ventricular fibrillation was induced with A.C. voltage. The heart was first defibrillated at an energy of 25 joules. The energy was lowered at 5 joule increments to determine a lower limit. The minimum energy required to defibrillate the heart was 5 joules.

EXAMPLE 3—HIGH POTENTIAL TEST

Each patch made in accordance with Example 1 was tested for electrical breakthrough. For this test, a flat sheet electrode connected to ground was used. An electrode patch was placed against the flat electrode. A half-inch diameter positive electrode was set on the inner metalized layer. An A.C. current of specified voltage was applied for one minute to the inner layer and measurements for breakthrough were measured on the exterior side of the outer layer. A range of voltage 50 V, 500 V, 800 V, and 1500 V were applied and no breakthrough was measured.

EXAMPLE 4—FLEX-TEST OF INNER METALIZED LAYER

The metalized membrane layer of the patch was made similar to that described in Example 1. The metalized membrane was attached to a stationary block on one end, and spring loaded ball slide on the other. Under the silicone pad was a two lobe cam mounted on a D.C. drive motor. The cam is positioned so that the silicone pad can be arched and relaxed repeatedly to simulate flex-testing of the metalized membrane. Resistance at predetermined intervals was measured by placing small plated disks on each end of the patch with probes attached to the disk and to a digital meter to measure changes in resistance.

The flex-tester was programmed to run about 56,000 cycles per hour. Resistance was found to increase from 1.0 to 100 ohms during the first hour and then to stabilize at 100 ohms for 500 hours.

It will be apparent to those skilled in the art that various modifications and variations can be made in the present invention. Thus, it is intended that the present invention cover modifications and variations of the invention provided that they come within the scope of the appended claims and their equivalents.

What is claimed is:

1. A patch electrode for use with defibrillators to stimulate an intended tissue comprising an outer, insulating membrane of porous expanded polytetrafluoroethylene, an inner metalized membrane, said inner membrane being of porous expanded polytetrafluoroethylene plated with a metal and having a metal surface; and means for bonding said inner membrane to said outer membrane so that a border of outer membrane surrounds and abuts said inner membrane.

2. The patch electrode of claim 1 wherein said inner membrane of expanded polytetrafluoroethylene has an average fibril length of greater than 30 microns and a thickness of at least 0.25 mm.

3. The patch electrode of claim 1 wherein said inner membrane of expanded polytetrafluoroethylene has an average fibril length of between 50 to 60 microns and a thickness of between 0.8 and 1.0 mm.

4. The patch electrode of claim 1 wherein said inner membrane has a metal plating of platinum.

5. The patch electrode of claim 1 wherein said inner membrane has a metal plating of gold.

6. The patch electrode of claim 1 wherein said outer membrane of expanded polytetrafluoroethylene has an average fibril length of about 10 microns and a thickness of less than 0.1 mm.

7. The patch electrode of claim 1 wherein said outer membrane of expanded polytetrafluoroethylene has a fibril length of less than 10 microns and a thickness of less than 0.08 mm.

8. The patch electrode of claim 1 having the shape of a tear drop.

9. The patch electrode of claim 1 having the shape of an hourglass.

10. The patch electrode of claim 1 having the shape of an inverted U.

11. The patch electrode of claim 1 wherein the means for bonding is an adhesive.

12. The patch electrode of claim 1 wherein the means for bonding is silicone.

13. A defibrillator system for delivering electrical shocks to the heart of a patient to restore cardiac rhythm comprising:
    (a) two subcutaneous patch electrodes for positioning inside the thoracic cavity proximate to the ventricles of the heart, each electrode comprising:
        (i) an outer insulating membrane of porous expanded polytetrafluoroethylene
        (ii) an inner membrane having a metal surface, said inner membrane being of porous expanded polytetrafluoroethylene plated with metal and bonded to said outer membrane,
    (b) two lead wires, each comprising a center conductor wire surrounded by at least one layer of insulation, each said lead wire adhesively affixed to a patch electrode by a conductive epoxy to form a conductive connection, said conductive connection further reinforced by a silicone boot; and
    (c) a pulse generator means having anode and cathode terminals to which said lead wires are connected.

14. The defibrillator system of claim 13 wherein each lead wire has two layers of expanded polytetrafluoroethylene insulation.

15. A defibrillator system for delivering electrical shocks to a muscle of a patient comprising:
    (a) two patch electrodes, each further comprising:
        (i) an outer insulating membrane of porous expanded polytetrafluoroethylene membrane,
        (ii) an inner membrane having a metal surface, and inner membrane being of porous expanded polytetrafluoroethylene plated with metal and bonded to said outer membrane,
    (b) two lead wires, each having a center conductor wire surrounded by at least one layer of insulation, each said lead wire adhesively affixed to a patch electrode by a conductive epoxy to form a conductive connection, said conductive connection further reinforced by a silicone boot; and
    (c) a pulse generator means having an anode and cathode terminal to which said lead wires are connected.

16. The defibrillator system of claim 15 wherein each lead wire has two layers of expanded polytetrafluoroethylene insulation.

* * * * *